US008629195B2

(12) United States Patent  
Schönberger et al.

(10) Patent No.: US 8,629,195 B2
(45) Date of Patent: Jan. 14, 2014

(54) PRODUCTION OF POLYURETHANE FOAMS

(75) Inventors: Jan Schönberger, Solingen (DE); Michael Mager, Leverkusen (DE); Thorsten Rische, Unna (DE); Sebastian Dörr, Düsseldorf (DE); Thomas Feller, Solingen (DE); Michael Heckes, Krefeld (DE); Melita Dietze, Erkrath (DE); Burkhard Fugmann, Ratingen (DE)

(73) Assignee: Bayer MaterialScience AG, Leverkusen (DE)

( * ) Notice: Subject to any disclaimer, the term of this patent is extended or adjusted under 35 U.S.C. 154(b) by 0 days.

(21) Appl. No.: 13/448,576

(22) Filed: Apr. 17, 2012

(65) Prior Publication Data

US 2012/0232006 A1    Sep. 13, 2012

Related U.S. Application Data

(63) Continuation-in-part of application No. 11/732,575, filed on Apr. 4, 2007, and a continuation of application No. 12/245,264, filed on Oct. 3, 2008, now abandoned.

(30) Foreign Application Priority Data

Apr. 8, 2006   (DE) .......................... 10 2006 016 636  
Oct. 5, 2007   (EP) ..................................... 07019525

(51) Int. Cl.
*C08J 9/30*      (2006.01)
*C08J 9/00*      (2006.01)
*C08J 9/28*      (2006.01)

(52) U.S. Cl.
USPC ........... 521/136; 521/137; 521/170; 521/172; 521/89; 602/46

(58) Field of Classification Search
USPC ..................... 521/137, 170, 172, 136; 602/46
See application file for complete search history.

(56) References Cited

U.S. PATENT DOCUMENTS

| 3,975,567 A | 8/1976 | Lock |
| 3,978,266 A | 8/1976 | Lock |
| 4,092,275 A | 5/1978 | Reischl et al. |
| 4,108,814 A | 8/1978 | Reiff et al. |
| 4,147,680 A | 4/1979 | Reischl et al. |
| 4,507,413 A | 3/1985 | Thoma et al. |
| 4,614,787 A | 9/1986 | Szycher et al. |
| 4,638,017 A | 1/1987 | Larson et al. |
| 4,655,210 A | 4/1987 | Edenbaum et al. |
| 4,675,232 A | 6/1987 | Edenbaum et al. |
| 4,690,953 A | 9/1987 | Orr et al. |
| 5,110,843 A | 5/1992 | Bries et al. |
| 5,147,338 A | 9/1992 | Lang et al. |
| 5,252,657 A | 10/1993 | Frankel et al. |
| 5,264,464 A | 11/1993 | Wishneski et al. |
| 5,389,718 A | 2/1995 | Potter et al. |
| 5,409,472 A | 4/1995 | Rawlings et al. |
| 5,604,267 A | 2/1997 | Duffy |
| 5,614,393 A | 3/1997 | Thomas et al. |
| 5,684,081 A | 11/1997 | Dannhorn et al. |
| 5,714,257 A | 2/1998 | Shah et al. |
| 5,763,067 A | 6/1998 | Bruggemann et al. |
| 5,914,125 A | 6/1999 | Andrews et al. |
| 6,020,390 A | 2/2000 | Leenslag |
| 6,034,149 A | 3/2000 | Bleys et al. |
| 6,043,411 A | 3/2000 | Nishizawa et al. |
| 6,103,358 A | 8/2000 | Bruggemann et al. |
| 6,187,832 B1 | 2/2001 | Leenslag |
| 6,271,276 B1 * | 8/2001 | Gribble et al. ............... 521/133 |
| 6,605,666 B1 | 8/2003 | Scholz et al. |
| 6,642,303 B2 | 11/2003 | Schutze et al. |
| 6,767,958 B2 | 7/2004 | Laas et al. |
| 6,890,551 B2 | 5/2005 | Lenz et al. |
| 7,538,154 B2 | 5/2009 | Pohl et al. |
| 7,893,320 B2 | 2/2011 | Cirpus et al. |
| 2001/0051165 A1 | 12/2001 | Lenz et al. |
| 2003/0105219 A1 | 6/2003 | Schutze et al. |
| 2004/0034162 A1 * | 2/2004 | Laas et al. ..................... 524/589 |
| 2004/0111763 A1 | 6/2004 | Heinz et al. |
| 2004/0116594 A1 | 6/2004 | Bhattacharjee et al. |
| 2004/0138319 A1 | 7/2004 | Taylor |
| 2004/0210026 A1 | 10/2004 | Mayer et al. |
| 2004/0241215 A1 | 12/2004 | Lipman |
| 2005/0037058 A1 | 2/2005 | Canada et al. |

(Continued)

FOREIGN PATENT DOCUMENTS

| CA | 1061043 A1 | 8/1979 |
| CA | 2189069 A1 | 12/1995 |

(Continued)

OTHER PUBLICATIONS

European Committee for Standardization, "Test Methods for Primary Wound Dressings. Part 1: Aspects of Absorbency," European Standard, Mar. 2002, Doc. EN 13726-1, DIN Deutsches Institut fur Normung e.V., pp. 1-14.

(Continued)

*Primary Examiner* — Randy Gulakowski
*Assistant Examiner* — Kara Boyle
(74) *Attorney, Agent, or Firm* — Novak Druce Connolly Bove + Quigg LLP

(57) ABSTRACT

The invention relates to a process for producing polyurethane foams, by frothing and drying mixtures of specific polyurethane dispersions and crosslinkers.

22 Claims, No Drawings

(56) References Cited

U.S. PATENT DOCUMENTS

| | | | |
|---|---|---|---|
| 2006/0128885 A1 | 6/2006 | Rische et al. | |
| 2007/0179210 A1* | 8/2007 | Swaniker | 521/172 |
| 2007/0254974 A1 | 11/2007 | Mager et al. | |
| 2007/0259984 A1 | 11/2007 | Dorr et al. | |
| 2007/0270730 A1 | 11/2007 | Rische et al. | |
| 2009/0092647 A1 | 4/2009 | Schoenberger et al. | |
| 2009/0263431 A1 | 10/2009 | Fugmann et al. | |
| 2010/0021514 A1 | 1/2010 | Fugmann | |

FOREIGN PATENT DOCUMENTS

| | | |
|---|---|---|
| CA | 2253119 A1 | 5/1999 |
| CA | 2378423 A1 | 1/2001 |
| CA | 2485060 A1 | 11/2003 |
| DE | 2264853 A1 | 7/1975 |
| DE | 2446440 A1 | 4/1976 |
| DE | 3526184 A1 | 2/1987 |
| DE | 19831285 A1 | 1/2000 |
| DE | 19836476 A1 | 2/2000 |
| DE | 19930526 A1 | 1/2001 |
| EP | 0059048 A1 | 9/1982 |
| EP | 0171268 A2 | 2/1986 |
| EP | 0235949 A1 | 9/1987 |
| EP | 0246723 A2 | 11/1987 |
| EP | 0541391 A1 | 5/1993 |
| EP | 0550162 A1 | 7/1993 |
| EP | 0753531 A1 | 1/1997 |
| EP | 0808859 A1 | 11/1997 |
| EP | 0916647 A2 | 5/1999 |
| EP | 916647 A2 | 5/1999 |
| EP | 1669382 A2 | 6/2006 |
| GB | 1462597 A | 1/1977 |
| JP | 2001-504150 A | 3/2001 |
| JP | 2006-111877 A | 4/2006 |
| WO | WO-91/13972 A1 | 9/1991 |
| WO | WO-93/06712 A1 | 4/1993 |
| WO | WO-93/11245 A1 | 6/1993 |
| WO | WO-94/11516 A1 | 5/1994 |
| WO | WO-94/18337 A1 | 8/1994 |
| WO | WO-94/23768 A1 | 10/1994 |
| WO | WO-95/18222 A1 | 7/1995 |
| WO | WO-95/32860 A1 | 12/1995 |
| WO | WO-96/21022 A2 | 7/1996 |
| WO | WO-97/21340 A1 | 6/1997 |
| WO | WO-97/30582 A1 | 8/1997 |
| WO | WO-9821258 A1 | 5/1998 |
| WO | WO-98/46763 A1 | 10/1998 |
| WO | WO-98/46764 A1 | 10/1998 |
| WO | WO-98/46765 A1 | 10/1998 |
| WO | WO-98/46776 A2 | 10/1998 |
| WO | WO-99/27111 A1 | 6/1999 |
| WO | WO-00/04069 A1 | 1/2000 |
| WO | WO-00/21557 A1 | 4/2000 |
| WO | WO-0074739 A1 | 12/2000 |
| WO | WO-01/02591 A1 | 1/2001 |
| WO | WO-01/59128 A2 | 8/2001 |
| WO | WO-01/88006 A1 | 11/2001 |
| WO | WO-02/26848 A2 | 4/2002 |
| WO | WO-0233001 A1 | 4/2002 |
| WO | WO-2006066752 A1 | 6/2006 |
| WO | WO-2007/089763 A2 | 8/2007 |

OTHER PUBLICATIONS

European Committee for Standarization, "Paints, Varnishes and Plastics—Determination of Non-Volatile-Matter Content," European Standard, Feb. 2008, Doc. EN ISO 3251, DIN Deutsches Institut fur Normung e.V., pp. 1-10.

German Standards, "Testing of Rubber—Determination of Tensile Strength at Break, Tensile Stress at Yield, Elongation at Break and Stress Values in a Tensile Test," Jul. 2008, Doc. No. 53504, DIN Deutsches Institue fur Normung e.V., pp. 1-7.

European Committee for Standardization, "Test Methods for Primary Wound Dressings. Part 2: Moisture Vapour Transmission Rate of Permeable Film Dressings," European Standard, Mar. 2002, Doc. EN 13726-2, DIN Deutsches Institute fur Normung e.V., pp. 1-7.

European Committee for Standardization, "Binders for Pains and Varnishes—Polyisocyanate Resins—General Methods of Test," European Standard, Feb. 2007, Doc. EN ISO 11901, DIN Deutsches Institute fur Normung e.V., pp. 1-8.

International Search Report of PCT/EP2008/007956 mailed Feb. 6, 2009.

* cited by examiner

PRODUCTION OF POLYURETHANE FOAMS

RELATED APPLICATIONS

This application claims benefit as a continuation-in-part to U.S. application Ser. No. 11/732,575, filed Apr. 4, 2007, and as a continuation to U.S. application Ser. No. 12/245,264, which are incorporated herein by reference in their entirety for all useful purposes. This application also claims benefit to German Patent Application No. 10 2006 016 636.1, filed on Apr. 8, 2006, and European Patent Application No. 07019525.0, filed Oct. 5, 2007 which are incorporated herein by reference in their entirety for all useful purposes.

BACKGROUND OF THE INVENTION

The invention relates to a process for producing polyurethane foams, by frothing and drying mixtures of specific polyurethane dispersions and crosslinkers.

In the field of wound management, the use of polyurethane foams as a wound contact layer is well known. The polyurethane foams used for this purpose are generally hydrophilic in order that good absorption of wound fluid may be ensured. Hydrophilic polyurethane foams are obtained by reaction of mixtures of diisocyanates and polyols, or NCO-functional polyurethane prepolymers, with water in the presence of certain catalysts and also (foam) additives. Aromatic diisocyanates are typically used, since they are best foamable. Numerous forms of these processes are known, for example described in U.S. Pat. Nos. 3,978,266, 3,975,567 and EP-A 0 059 048. However, the aforementioned processes have the disadvantage that they require the use of reactive mixtures, containing diisocyanates or corresponding prepolymers, whose handling is technically inconvenient and costly, since appropriate protective measures are necessary for example.

It is also known to produce foams from polyurethane dispersions by incorporating air in the presence of suitable (foam) additives by vigorous stirring. So-called mechanical polyurethane foams are obtained after drying and curing. In connection with wound dressings, such foams are described in EP-A 0 235 949 and EP-A 0 246 723, the foam either having a self-adherent polymer added to it, or being applied to a film of a self-adherent polymer. The use of the foams as such, i.e. without self-adherent polymers, is not described. In addition, the examples recited in EP-A 0 235 949 and EP-A 0 246 723 mandate the use as crosslinkers of polyaziridines which should now only be used in a limited way because of their toxicity. U.S. Pat. No. 4,655,210 describes the use of the aforementioned mechanical foams for wound dressings having a specific construction of backing, foam and skin contact layer.

The polyurethane dispersions described in EP-A 0 235 949, EP-A 0 246 723 and U.S. Pat. No. 4,655,210 are anionically hydrophilicized through incorporation of certain carboxylic acids such as dimethylol carboxylic acids and neutralization of the carboxylic acids with tertiary amines, for example triethylamine. However, the ammonium carboxylates thus formed are decomposable, in particular at higher temperatures, which sets the amines free again. This is an immense disadvantage in relation to the processing of such products and particularly in skin contact. Furthermore, these polyurethane dispersions were produced using the dimethylol carboxylic acids in dissolved form, for example in dimethylformamide or N-methylpyrrolidone, as a result of which the final products have altogether a high VOC content, 10.8 g litre (without water) in the case of the Witcobond™ 290 H used.

EP 0 760 743 describes such mechanical foams formed on the basis of latex dispersions, but they do not consist of polyurethanes and have worse mechanical properties.

The present invention therefore has for its object to provide novel wound dressings which are based on polyurethanes and are obtainable in a very simple manner and without the use of such building block components or additives as are not generally recognized as safe. It is a further prerequisite that these wound dressings have good mechanical properties, a high uptake capacity for physiological saline and also a high water vapour transmission rate. Moreover, the foams should have a satisfactory water resistance.

EMBODIMENTS OF THE INVENTION

An embodiment of the present invention is a process for producing foamed articles comprising frothing and drying a composition comprising aqueous polyurethane dispersions (I) anionically hydrophilicized by means of sulphonate groups and a crosslinker (II) wherein at least partial chemical crosslinking occurs in said process.

Another embodiment of the present invention is the above process, wherein said foamed articles are wound dressings.

Another embodiment of the present invention is the above process, wherein said polyurethane dispersion (I) are anionically hydrophilicized by sulphonate groups only.

Another embodiment of the present invention is the above process, wherein said sulphonate groups have alkali metal cations as counter-ions.

Another embodiment of the present invention is the above process, wherein said polyurethane dispersion (I) comprise 0.1 to 15 milliequivalents per 100 g of solid resin of anionic or potentially anionic groups based on solid resin.

Another embodiment of the present invention is the above process, wherein said polyurethane dispersion (I) have solids contents in the range of from 55% to 65% by weight based on the polyurethane present therein.

Another embodiment of the present invention is the above process, wherein said polyurethane dispersion (I) is prepared by A) producing a isocyanate-functional prepolymer from A1) organic polyisocyanates; A2) polymeric polyols having number-average molecular weights in the range from 400 to 8000 g/mol and OH functionalities in the range from 1.5 to 6; and A3) optionally hydroxyl-functional compounds having molecular weights in the range from 62 to 399 g/mol; and A4) optionally isocyanate-reactive, anionic or potentially anionic and optionally nonionic hydrophilicizing agents; and B) wholly or partly reacting the free NCO groups of said isocyanate-functional prepolymer B1) optionally with amino-functional compounds having molecular weights in the range from 32 to 400 g/mol; and B2) with amino-functional, anionic or potentially anionic hydrophilicizing agents by chain extension; wherein said isocyanate-functional prepolymer is dispersed in water before, during or after step B).

Another embodiment of the present invention is the above process, wherein said crosslinkers (II) are selected from the group consisting of unblocked, optionally hydrophilicized polyisocyanates; - and amine-formaldehyde resins; phenolic resins; aldehyde and ketone resins; resols; furan resins; urea resins; carbamidic ester resins; triazine resins; melamine resins; benzoguanamine resins; cyanamide resins; and aniline resins.

Another embodiment of the present invention is the above process, wherein said crosslinkers (II) are unblocked polyisocyanates.

Another embodiment of the present invention is the above process, wherein said unblocked polyisocyanates are hydrophilicized.

Another embodiment of the present invention is the above process, further comprising auxiliary and additive materials (III).

Another embodiment of the present invention is the above process, wherein said auxiliary and additive materials (III) are foam formers and stabilizers selected from the group consisting of fatty acid amides, sulphosuccinamides, hydrocarbyl sulphonates or sulphates, alkyl polyglycosides, EO-PO block copolymers, fatty acid salts, and combinations thereof.

Another embodiment of the present invention is the above process, wherein said foam formers and stabilizers are EO-PO block copolymers. The process of claim 1, further comprising active components selected from the group consisting of antiseptics, growth factors, protease inhibitors, and nonsteroidal anti-inflammatories/opiates.

Another embodiment of the present invention is the above process, wherein said active component is an antiseptic biguanide and/or its salt.

Yet another embodiment of the present invention is a foamed article prepared by the above process.

Another embodiment of the present invention is the above foamed article, wherein said foamed article has a microporous, open-cell structure and a density of below 0.4 g/cm$^3$ in the dried state.

Another embodiment of the present invention is the above foamed article, wherein said foamed article has a DIN EN 13726-1 Part 3.2 physiological saline absorbency in the range from 100 to 1500% (mass of liquid taken up, based on the mass of dry foam) and a DIN EN 13726-2 Part 3.2 water vapour transmission rate in the range from 2000 to 8000 g/24 h*m$^2$.

Another embodiment of the present invention is the above foamed article, wherein said foamed article further comprises an active component.

Another embodiment of the present invention is the above foamed article, wherein said foamed article is a wound dressing.

Yet another embodiment of the present invention is a composition comprising as aqueous polyurethane dispersion (I) anionically hydrophilicized by means of sulphonate groups and a crosslinker (II).

Another embodiment of the present invention is the above composition, further comprising an active component selected from the group consisting of antiseptics, growth factors, protease inhibitors, and nonsteroidal anti-inflammatories/opiates.

Another embodiment of the present invention is the above composition, wherein said active component is an antiseptic biguanide and/or its salt.

DESCRIPTION OF THE INVENTION

It has now been found that such polyurethane-based wound dressings are obtainable wherein compositions containing specific aqueous polyurethane dispersions and crosslinkers are frothed and then dried with at least partial crosslinking.

The present invention accordingly provides a process for producing foamed articles, preferably wound dressings which comprises compositions containing aqueous polyurethane dispersions (I) anionically hydrophilicized by means of sulphonate groups being frothed together with crosslinkers (II) and dried with at least partial chemical crosslinking.

Crosslinking herein is to be understood as meaning the formation of covalent bonds between reactive groups of the crosslinker and the polyurethanes contained in the polyurethane dispersions.

Polyurethane foam wound dressings for the purposes of the present invention are porous materials, preferably having at least some open-cell content, which consist essentially of polyurethanes and protect wounds against germs and environmental influences like a sterile covering, have a fast and high absorbance of physiological saline or to be more precise wound fluid, have a suitable permeability for moisture to ensure a suitable wound climate, and have sufficient mechanical strength.

Preferably, these dispersions have sulphonate groups only for the anionic hydrophilicization.

Preferably, the specific polyurethane dispersions (I) have a low degree of hydrophilic anionic groups, preferably 0.1 to 15 milliequivalents per 100 g of polyurethane (solid resin).

To achieve good stability to sedimentation, the number average particle size of the specific polyurethane dispersions is preferably less than 750 nm and more preferably less than 500 nm, determined by laser correlation spectroscopy.

The solids contents of the polyurethane dispersions (I) are preferably in the range from 30% to 70% by weight, more preferably in the range from 50% to 70% by weight and most preferably in the range from 55% to 65% by weight and in particular in the range from 60% to 65% by weight, based on the polyurethane present therein.

The level of unbound organic amines in these polyurethane dispersions is preferably less than 0.5% by weight and more preferably less than 0.2% by weight, based on the entire dispersions.

Such preferred polyurethane dispersions (I) are obtainable by

A) isocyanate-functional prepolymers being produced from
  A1) organic polyisocyanates
  A2) polymeric polyols having number-average molecular weights in the range from 400 to 8000 g/mol, preferably in the range from 400 to 6000 g/mol and even more preferably in the range from 600 to 3000 g/mol and OH functionalities in the range from 1.5 to 6, preferably in the range from 1.8 to 3 and more preferably in the range from 1.9 to 2.1, and
  A3) optionally hydroxyl-functional compounds having molecular weights in the range from 62 to 399 g/mol and
  A4) optionally isocyanate-reactive, anionic or potentially anionic and/or optionally nonionic hydrophilicizing agents
  and
B) its free NCO groups then being wholly or partly reacted
  B1) optionally with amino-functional compounds having molecular weights in the range from 32 to 400 g/mol and
  B2) with amino-functional, anionic or potentially anionic hydrophilicizing agents
by chain extension, and the prepolymers being dispersed in water before, during or after step B).

If desired, the prepolymer can be wholly or partly converted into the anionic form by admixing a base, before, during or after dispersion.

To achieve anionic hydrophilicization, A4) and/or B2) shall utilize hydrophilicizing agents that have at least one NCO-reactive group such as amino, hydroxyl or thiol groups and additionally have —COO$^-$or —SO$_3^-$or —PO$_3^{2-}$as anionic groups or their wholly or partly protonated acid forms as potentially anionic groups.

Preferably, A4) and/or B2) utilize such compounds for anionic or potentially anionic hydrophilicization as have exclusively sulphonic acid or sulphonate groups (—$SO_3H$ or —$SO_3M$, where M=alkali metal or alkaline earth metal) as anionic or potentially anionic functionality.

Suitable polyisocyanates of component A1) are the well-known aliphatic or cycloaliphatic polyisocyanates having an NCO functionality of not less than 2.

Examples of such suitable polyisocyanates are 1,4-butylene diisocyanate, 1,6-hexa-methylene diisocyanate (HDI), isophorone diisocyanate (IPDI), 2,2,4- and/or 2,4,4-trimethylhexamethylene diisocyanate, the isomeric bis(4,4'-isocyanato-cyclohexyl)methane or their mixtures of any desired isomer content, 1,4-cyclo-hexylene diisocyanate, 4-isocyanatomethyl-1,8-octane diisocyanate (nonane triisocyanate) and also alkyl 2,6-diisocyanatohexanoates (lysine diisocyanates) having C1-C8-alkyl groups.

As well as the aforementioned polyisocyanates, it is possible to use modified diisocyanates having a functionality≥2 and a uretidione, isocyanurate, urethane, allophanate, biuret, iminooxadiazinedione or oxadiazinetrione structure, and also mixtures thereof pro rata.

Preferably, the polyisocyanates or polyisocyanate mixtures of the aforementioned type have exclusively aliphatically or cycloaliphatically attached isocyanate groups or mixtures thereof and an average NCO functionality in the range from 2 to 4, preferably in the range from 2 to 2.6 and more preferably in the range from 2 to 2.4, for the mixture.

It is particularly preferable for A1) to utilize hexamethylene diisocyanate, isophorone diisocyanate or the isomeric bis(4,4'-isocyanatocyclohexyl)methanes and also mixtures thereof.

A2) utilizes polymeric polyols having a number average molecular weight $M_n$ in the range from 400 to 8000 g/mol, preferably from 400 to 6000 g/mol and more preferably from 600 to 3000 g/mol. These preferably have an OH functionality in the range from 1.5 to 6, more preferably in the range from 1.8 to 3 and most preferably in the range from 1.9 to 2.1.

Such polymeric polyols are the well-known polyurethane coating technology polyester polyols, polyacrylate polyols, polyurethane polyols, polycarbonate polyols, polyether polyols, polyester polyacrylate polyols, polyurethane polyacrylate polyols, polyurethane polyester polyols, polyurethane polyether polyols, polyurethane polycarbonate polyols and polyester polycarbonate polyols. These can be used in A2) individually or in any desired mixtures with one another.

Such polyester polyols are the well-known polycondensates formed from di- and also optionally tri- and tetraols and di- and also optionally tri- and tetracarboxylic acids or hydroxy carboxylic acids or lactones. Instead of the free polycarboxylic acids it is also possible to use the corresponding polycarboxylic anhydrides or corresponding polycarboxylic esters of lower alcohols for preparing the polyesters.

Examples of suitable diols are ethylene glycol, butylene glycol, diethylene glycol, triethylene glycol, polyalkylene glycols such as polyethylene glycol, also 1,2-propanediol, 1,3-propanediol, butanediol(1,3), butanediol(1,4), hexanediol(1,6) and isomers, neopentyl glycol or neopentyl glycol hydroxypivalate, of which hexanediol(1,6) and isomers, butanediol(1,4), neopentyl glycol and neopentyl glycol hydroxypivalate are preferred. Besides these it is also possible to use polyols such as trimethylolpropane, glycerol, erythritol, pentaerythritol, trimethylbenzene or trishydroxyethyl isocyanurate.

Useful dicarboxylic acids include phthalic acid, isophthalic acid, terephthalic acid, tetrahydrophthalic acid, hexahydrophthalic acid, cyclohexanedicarboxylic acid, adipic acid, azelaic acid, sebacic acid, glutaric acid, tetrachlorophthalic acid, maleic acid, fumaric acid, itaconic acid, malonic acid, suberic acid, 2-methylsuccinic acid, 3,3-diethyl glutaric acid and/or 2,2-dimethylsuccinic acid. The corresponding anhydrides can also be used as a source of an acid.

When the average functionality of the polyol to be esterified is >than 2, monocarboxylic acids, such as benzoic acid and hexanecarboxylic acid can be used as well in addition.

Preferred acids are aliphatic or aromatic acids of the aforementioned kind. Adipic acid, isophthalic acid and phthalic acid are particularly preferred.

Hydroxy carboxylic acids useful as reaction participants in the preparation of a polyester polyol having terminal hydroxyl groups include for example hydroxy-caproic acid, hydroxybutyric acid, hydroxydecanoic acid, hydroxystearic acid and the like. Suitable lactones include caprolactone, butyrolactone and homologues. Caprolactone is preferred.

A2) may likewise utilize hydroxyl-containing polycarbonates, preferably polycarbonatediols, having number average molecular weights $M_n$, in the range from 400 to 8000 g/mol and preferably in the range from 600 to 3000 g/mol. These are obtainable by reaction of carbonic acid derivatives, such as diphenyl carbonate, dimethyl carbonate or phosgene, with polyols, preferably diols.

Examples of such diols are ethylene glycol, 1,2-propanediol, 1,3-propanediol, 1,3-butanediol, 1,4-butanediol, 1,6-hexanediol, 1,8-octanediol, neopentyl glycol, 1,4-bishydroxymethylcyclohexane, 2-methyl-1,3-propanediol, 2,2,4-trimethyl-1,3-pentanediol, dipropylene glycol, polypropylene glycols, dibutylene glycol, poly-butylene glycols, bisphenol A and lactone-modified diols of the aforementioned kind.

The diol component preferably contains 40% to 100% by weight of hexanediol, preference being given to 1,6-hexanediol and/or hexanediol derivatives. Such hexanediol derivatives are based on hexanediol and have ester or ether groups as well as terminal OH groups. Such derivatives are obtainable by reaction of hexanediol with excess caprolactone or by etherification of hexanediol with itself to form di- or trihexylene glycol.

In lieu of or in addition to pure polycarbonate diols, polyether-polycarbonate diols can also be used in A2).

Hydroxyl-containing polycarbonates preferably have a linear construction.

A2) may likewise utilize polyether polyols.

Useful polyether polyols include for example the well-known polyurethane chemistry polytetramethylene glycol polyethers as are obtainable by polymerization of tetrahydrofuran by means of cationic ring opening.

Useful polyether polyols likewise include the well-known addition products of styrene oxide, ethylene oxide, propylene oxide, butylene oxides and/or epichlorohydrin onto di- or polyfunctional starter molecules. Polyether polyols based on the at least proportional addition of ethylene oxide onto di- or polyfunctional starter molecules can also be used as component A4) (nonionic hydrophilicizing agents).

Useful starter molecules include all prior art compounds, for example water, butyl diglycol, glycerol, diethylene glycol, trimethylolpropane, propylene glycol, sorbitol, ethylenediamine, triethanolamine, 1,4-butanediol.

A3) may utilize polyols of the specified molecular weight range with up to 20 carbon atoms, such as ethylene glycol, diethylene glycol, triethylene glycol, 1,2-propanediol, 1,3-propanediol, 1,4-butanediol, 1,3-butylene glycol, cyclohexanediol, 1,4-cyclohexanedimethanol, 1,6-hexanediol, neopentyl glycol, hydroquinone dihydroxyethyl ether, bisphenol A (2,2-bis(4-hydroxyphenyl)propane), hydrogenated bisphenol A, (2,2-bis(4-hydroxycyclohexyl)propane), trimethylolpropane, glycerol, pentaerythritol and also any desired mixtures thereof with one another.

Also suitable are esterdiols of the specified molecular weight range such as α-hydroxybutyl-ε-hydroxycaproic acid ester, ω-hydroxyhexyl-γ-hydroxybutyric acid ester, β-hydroxyethyl adipate or bis(β-hydroxyethyl)terephthalate.

A3) may further utilize monofunctional isocyanate-reactive hydroxyl-containing compounds. Examples of such monofunctional compounds are ethanol, n-butanol, ethylene glycol monobutyl ether, diethylene glycol monomethyl ether, diethylene glycol monobutyl ether, propylene glycol monomethyl ether, dipropylene glycol monomethyl ether, tripropylene glycol monomethyl ether, dipropylene glycol monopropyl ether, propylene glycol monobutyl ether, dipropylene glycol monobutyl ether, tripropylene glycol monobutyl ether, 2-ethylhexanol, 1-octanol, 1-dodecanol, 1-hexadecanol.

Useful anionically hydrophilicizing compounds for component A4) include salts of mono- and dihydroxy sulphonic acids. Examples of such anionic hydrophilicizing agents are the adduct of sodium bisulphite onto 2-butene-1,4-diol as described in DE-A 2 446 440, pages 5-9, formula I-III.

Useful nonionically hydrophilicizing compounds for component A4) include for example polyoxyalkylene ethers containing at least one hydroxyl, amino or thiol group. Examples are the monohydroxyl-functional polyalkylene oxide polyether alcohols containing on average 5 to 70 and preferably 7 to 55 ethylene oxide units per molecule and obtainable in a conventional manner by alkoxylation of suitable starter molecules (for example in Ullmanns Encyclopädie der technischen Chemie, 4th edition, volume 19, Verlag Chemie, Weinheim pages 31-38). These are either pure polyethylene oxide ethers or mixed polyalkylene oxide ethers, containing at least 30 mol % and preferably at least 40 mol % of ethylene oxide units, based on all alkylene oxide units present.

Particularly preferred nonionic compounds are monofunctional mixed polyalkylene oxide polyethers having 40 to 100 mol % of ethylene oxide units and 0 to 60 mol % of propylene oxide units.

Useful starter molecules for such nonionic hydrophilicizing agents include saturated monoalcohols such as methanol, ethanol, n-propanol, isopropanol, n-butanol, isobutanol, sec-butanol, the isomers pentanols, hexanols, octanols and nonanols, n-decanol, n-dodecanol, n-tetradecanol, n-hexadecanol, n-octadecanol, cyclohexanol, the isomeric methylcyclohexanols or hydroxymethylcyclohexane, 3-ethyl-3-hydroxymethyloxetane or tetrahydrofurfuryl alcohol, diethylene glycol monoalkyl ethers, for example diethylene glycol monobutyl ether, unsaturated alcohols such as allyl alcohol, 1,1-dimethylallyl alcohol or oleic alcohol, aromatic alcohols such as phenol, the isomeric cresol or methoxyphenols, araliphatic alcohols such as benzyl alcohol, anisal alcohol or cinnamyl alcohol, secondary monoamines such as dimethylamine, diethylamine, dipropylamine, diisopropylamine, dibutylamine, bis(2-ethylhexyl)amine, N-methylcyclohexylamine, N-ethylcyclohexylamine or dicyclo-hexylamine and also heterocyclic secondary amines such as morpholine, pyrrolidine, piperidine or 1H pyrazole. Preferred starter molecules are saturated monoalcohols of the aforementioned kind. Particular preference is given to using diethylene glycol monobutyl ether or n-butanol as starter molecules.

Useful alkylene oxides for the alkoxylation reaction are in particular ethylene oxide and propylene oxide, which can be used in any desired order or else in admixture in the alkoxylation reaction.

Component B1) may utilize organic di- or polyamines such as for example 1,2-ethylenediamine, 1,2-diaminopropane, 1,3-diaminopropane, 1,4-diaminobutane, 1,6-diaminohexane, isophoronediamine, isomeric mixture of 2,2,4- and 2,4,4-tri-methylhexamethylenediamine, 2-methylpentamethylenediamine, diethylenetriamine, 4,4-diaminodicyclohexylmethane and/or dimethylethylenediamine.

Component B1) can further utilize compounds which as well as a primary amino group also have secondary amino groups or which as well as an amino group (primary or secondary) also have OH groups. Examples thereof are primary/secondary amines, such as diethanolamine, 3-amino-1-methylaminopropane, 3-amino-1-ethylaminopropane, 3-amino-1-cyclohexylaminopropane, 3-amino-1-methylaminobutane, alkanolamines such as N-aminoethylethanolamine, ethanolamine, 3-aminopropanol, neopentanolamine.

Component B1) can further utilize monofunctional isocyanate-reactive amine compounds, for example methylamine, ethylamine, propylamine, butylamine, octylamine, laurylamine, stearylamine, isononyloxypropylamine, dimethylamine, diethylamine, dipropylamine, dibutylamine, N-methylaminopropylamine, diethyl(methyl)aminopropylamine, morpholine, piperidine, or suitable substituted derivatives thereof, amide-amines formed from diprimary amines and monocarboxylic acids, monoketime of diprimary amines, primary/tertiary amines, such as N,N-dimethylaminopropylamine.

Useful anionically hydrophilicizing compounds for component B2) include alkali metal salts of the mono- and diamino sulphonic acids. Examples of such anionic hydrophilicizing agents are salts of 2-(2-aminoethylamino)ethanesulphonic acid, ethylenediaminepropylsulphonic acid, ethylenediaminebutylsulphonic acid, 1,2- or 1,3-propylenediamine-β-ethylsulphonic acid or taurine. It is further possible to use the salt of cyclohexylaminopropanesulphonic acid (CAPS) from WO-A 01/88006 as an anionic hydrophilicizing agent.

Particularly preferred anionic hydrophilicizing agents B2) are those which contain sulphonate groups as ionic groups and two amino groups, such as the salts of 2-(2-aminoethylamino)ethylsulphonic acid and 1,3-propylenediamine-β-ethylsulphonic acid.

Mixtures of anionic and nonionic hydrophilicizing agents can also be used.

A preferred embodiment for producing the specific polyurethane dispersions utilizes components A1) to A4) and B1) to B2) in the following amounts, the individual amounts always adding up to 100% by weight:

5% to 40% by weight of component A1),
55% to 90% by weight of A2),
0.5% to 20% by weight of the sum total of components A3) and B1)
0.1% to 25% by weight of the sum total of the components A4) and B2), with 0.1 to 5% by weight of anionic or potentially anionic hydrophilicizing agents from A4) and/or B2) being used, based on the total amount of components A1) to A4) and B1) to B2).

A particularly preferred embodiment for producing the specific polyurethane dispersions utilizes components A1) to A4) and B1) to B2) in the following amounts, the individual amounts always adding up to 100% by weight:

5% to 35% by weight of component A1),
60% to 90% by weight of A2),
0.5% to 15% by weight of the sum total of components A3) and B1)
0.1% to 15% by weight of the sum total of the components component A4) and B2), with 0.2 to 4% by weight of anionic or potentially anionic hydrophilicizing agents from A4) and/or B2) being used, based on the total amount of components A1) to A4) and B1) to B2).

A very particularly preferred embodiment for producing the specific polyurethane dispersions utilizes components A1) to A4) and B1) to B2) in the following amounts, the individual amounts always adding up to 100% by weight:

10% to 30% by weight of component A1),
65% to 85% by weight of A2),
0.5% to 14% by weight of the sum total of components A3) and B1)
0.1% to 13.5% by weight of the sum total of the components A4) and B2), with 0.5 to 3.0% by weight of anionic or potentially anionic hydrophilicizing agents from A4) and/or B2) being used, based on the total amount of components A1) to A4) and B1) to B2).

The production of the specific polyurethane dispersions can be carried out in one or more stages in homogeneous phase or, in the case of a multistage reaction, partly in disperse phase. After completely or partially conducted polyaddition from A1) to A4) a dispersing, emulsifying or dissolving step is carried out. This is followed if appropriate by a further polyaddition or modification in disperse phase.

Any prior art process can be used, examples being the prepolymer mixing process, the acetone process or the melt dispersing process. The acetone process is preferred.

Production by the acetone process typically involves the constituents A2) to A4) and the polyisocyanate component A1) being to produce an isocyanate-functional polyurethane prepolymer wholly or partly introduced as an initial charge and optionally diluted with a water-miscible but isocyanate-inert solvent and heated to temperatures in the range from 50 to 120° C. The isocyanate addition reaction can be speeded using the catalysts known in polyurethane chemistry.

Useful solvents include the customary aliphatic, keto-functional solvents such as acetone, 2-butanone, which can be added not just at the start of the production process but also later, optionally in portions. Acetone and 2-butanone are preferred and acetone is particularly preferred.

Subsequently, any constituents of A1) to A4) not added at the start of the reaction are added.

In the production of the polyurethane prepolymer from A1) to A4), the amount of substance ratio of isocyanate groups to isocyanate-reactive groups is in the range from 1.05 to 3.5, preferably in the range from 1.1 to 3.0 and more preferably in the range from 1.1 to 2.5.

The reaction of components A1) to A4) to form the prepolymer is effected partially or completely, but preferably completely. Polyurethane prepolymers containing free isocyanate groups are obtained in this way, without a solvent or in solution.

Subsequently, in a further process step, the prepolymer obtained is dissolved with the aid of aliphatic ketones such as acetone or 2-butanone, if this has not been done yet or only to some extent.

In the chain extension of step B), $NH_2$— and/or NH-functional components are reacted with the still remaining isocyanate groups of the prepolymer. Preferably, the chain extension/termination is carried out before dispersion in water.

Useful chain-extending components include organic di- or polyamines B1) such as for example ethylenediamine, 1,2-diaminopropane, 1,3-diaminopropane, 1,4-diaminobutane, 1,6-diaminohexane, isophoronediamine, isomeric mixture of 2,2,4- and 2,4,4-trimethylhexamethylenediamine, 2-methylpentamethylenediamine, diethylenetriamine, diaminodicyclohexylmethane and/or dimethylethylendiamine.

In addition, it is also possible to employ compounds B1) which, as well as a primary amino group, also have secondary amino groups or which have OH groups as well as an amino group (primary or secondary). Examples thereof are primary/secondary amines, such as diethanolamine, 3-amino-1-methylaminopropane, 3-amino-1-ethyl-aminopropane, 3-amino-1-cyclohexylaminopropane, 3-amino-1-methylaminobutane, alkanolamines such as N-aminoethylethanolamine, ethanolamine, 3-aminopropanol, neopentanolamine for chain extension or termination.

Chain termination is typically carried out using amines B1) having an isocyanate-reactive group such as methylamine, ethylamine, propylamine, butylamine, octylamine, laurylamine, stearylamine, isononyloxypropylamine, dimethylamine, diethylamine, dipropylamine, dibutylamine, N-methylaminopropylamine, diethyl-(methyl)aminopropylamine, morpholine, piperidine or suitable substituted derivatives thereof, amide amines formed from diprimary amines and mono-carboxylic acids, monoketimes of diprimary amines, primary/tertiary amines, such as N,N-dimethylaminopropylamine.

When chain extension is carried out using anionic hydrophilicizing agents conforming to definition B2) with $NH_2$ or NH groups, the chain extension of the prepolymers is preferably carried out before dispersion.

The degree of chain extension, i.e. the equivalent ratio of NCO-reactive groups of the compounds used for chain extension and chain termination to free NCO groups of the prepolymer, is between 40 and 150%, preferably between 50 and 120% and more preferably between 60 and 120%.

The aminic components B1) and B2) can optionally be used in water- or solvent-diluted form in the process of the present invention, individually or in mixtures, any order of addition being possible in principle.

When water or organic solvent is used as a diluent, the diluent content of the chain-extending component used in B) is preferably in the range from 70% to 95% by weight.

Dispersion is preferably carried out following chain extension. For dispersion, the dissolved and chain-extended polyurethane polymer is either introduced into the dispersing water, if appropriate by substantial shearing, such as vigorous stirring for example, or conversely the dispersing water is stirred into the chain-extended polyurethane polymer solutions. It is preferable to add the water to the dissolved chain-extended polyurethane polymer.

The solvent still present in the dispersions after the dispersing step is then typically removed by distillation. Removal during the dispersing step is likewise possible.

The residual level of organic solvents in the dispersions which are essential to the present invention is typically less than 1% by weight and preferably less than 0.5% by weight, based on the entire dispersion.

The pH of the dispersions which are essential to the present invention is typically less than 8.0, preferably less than 7.5 and more preferably between 5.5 and 7.5.

Useful crosslinkers (II) include in principle any organic, at least difunctional compounds which, under the stated drying conditions, form covalent bonds with the employed polyurethane of polyurethane dispersion (I) and thus lead to the desired improvement in the mechanical properties and/or in water resistance. Examples of such crosslinkers are unblocked, optionally hydrophilicized polyisocyanates, amide- and amine-formaldehyde resins, phenolic resins, aldehyde and ketone resins, such as phenol-formaldehyde resins, resols, furan resins, urea resins, carbamidic ester resins, triazine resins, melamine resins, benzoguanamine resins, cyanamide resins and aniline resins.

Preference for use as crosslinkers is given to unblocked polyisocyanates or melamine resins, more preferably unblocked polyisocyanates and most preferably hydrophilicized polyisocyanates, which are particularly easy to incorporate in the polyurethane dispersion (I) by any common mixing and dispersing techniques.

It is also possible to use mixtures of various crosslinkers of component (II).

As well as the dispersions (I) and the crosslinkers (II), the compositions to be frothed may also contain auxiliary and additive materials (III).

Examples of such auxiliary and additive materials (III) are foam auxiliaries such as foam formers and stabilizers, thickeners or thixotroping agents, antioxidants, light stabilizers, emulsifiers, plasticizers, pigments, fillers and flow control agents.

Preferably, foam auxiliaries such as foam formers and stabilizers are included as auxiliary and additive materials (III). Useful foam auxiliaries include commercially available compounds such as fatty acid amides, hydrocarbyl sulphates or sulphonates or fatty acid salts, in which case the lipophilic radical preferably contains 12 to 24 carbon atoms, and also alkyl polyglycosides obtainable in a conventional manner by reaction of comparatively long-chain monoalcohols (4 to 22 carbon atoms in the alkyl radical) with mono-, di- or polysaccharides (see for example Kirk-Othmer, Encyclopedia of Chemical Technology, John Wiley & Sons, Vol. 24, p. 29).

Particularly suitable foam auxiliaries are EO-PO block copolymers obtainable in a conventional manner by addition of ethylene oxide and propylene oxide onto OH— or NH— functional starter molecules (see for example Kirk-Othmer, Encyclopedia of Chemical Technology, John Wiley & Sons, Vol. 24, p. 28). To improve foam formation, foam stability or the properties of the resulting polyurethane foam further additives may be present in component (III) as well as the EO-PO block copolymers.

Such further additives may in principle be any anionic, nonionic or cationic surfactant known per se. Preferably, however, only the EO-PO block copolymers are used as component (III).

Commercially available thickeners can be used, such as derivatives of dextrin, of starch or of cellulose, examples being cellulose ethers or hydroxyethylcellulose, polysaccharide derivatives such as gum arabic, organic wholly synthetic thickeners based on polyacrylic acids, polyvinylpyrrolidones, polymethacrylic compounds or polyurethanes (associative thickeners) and also inorganic thickeners, such as bentonites or silicas.

The compositions which are essential to the present invention typically contain, based on dry substance, 90 to 99.9 parts by weight of polyurethane dispersion (I), 0.1 to 10 parts by weight of crosslinker (II) and 0 to 10 parts by weight of foam auxiliary (III). Preferably, the compositions which are essential to the present invention contain, based on the dry substance, 87.5 to 98.9 parts by weight of dispersion (I), 0.1 to 5 parts by weight of crosslinker (II) and 1 to 7.5 parts by weight of foam auxiliary (III), more preferably 90.5 to 97 parts by weight of dispersion (I), 0.5 to 2 parts by weight of crosslinker (II) and 2.5 to 7.5 by parts by weight of foam auxiliary (based on the dry substance).

Frothing in the process of the present invention is accomplished by mechanical stirring of the composition at high speeds of rotation, by shaking or by decompressing a blowing gas.

Mechanical frothing can be effected using desired mechanical stirring, mixing and dispersing techniques. Air is generally introduced, but nitrogen and other gases can also be used for this purpose.

The foam thus obtained is, in the course of frothing or immediately thereafter, applied to a substrate or introduced into a mould and dried.

Application to a substrate can be for example by pouring or blade coating, but other conventional techniques are also possible. Multilayered application with intervening drying steps is also possible in principle. Application and drying can each be carried out batchwise or continuously, but the entirely continuous process is preferred.

Useful substrates include papers (e.g. release papers) or films which facilitate simple detachment of the wound dressing before it is used to cover an injured site. Drying is generally effected using conventional heating and drying apparatus, such as (circulating air) drying cabinets, hot air or IR radiators, typically at elevated temperatures of 30 to 200° C., preferably 100 to 170° C. and more preferably 110 to 160° C. Preference is also given to an at least two-stage drying operation beginning at temperatures of 110 to 130° C. and with subsequence further drying (crosslinking) at elevated temperatures of 130 to 160° C.

The formation of covalent bonds between the crosslinker (II) and the polyurethane of the polyurethane dispersion (I) similarly takes place during drying. This provides improved water resistance and/or an improvement in the mechanical properties.

The present invention further provides the wound dressings obtainable by the process of the present invention.

Before drying, the foam densities of the wound dressings are typically in the range from 50 to 800 g/litre, preferably in the range from 100 to 500 g/litre and more preferably in the range from 100 to 250 g/litre (mass of all input materials [in g] based on the foam volume of one litre).

After drying, the wound dressings have a microporous, open-cell structure comprising intercommunicating cells. The density of the dried foams is typically below 0.4 g/cm$^3$, preferably below 0.35 g/cm$^3$, more preferably it is in the range from 0.01 to 0.3 g/cm$^3$ and most preferably in the range from 0.1 to 0.3 g/cm$^3$.

The DIN EN 13726-1 Part 3.2 absorbency with regard to physiological saline is typically in the range from 100 to 1500%, preferably in the range from 300 to 1500% and most preferably in the range from 300 to 800% for the polyurethane foams (mass of absorbed liquid based on the mass of dry foam). The DIN EN 13726-2 Part 3.2 water vapour transmission rate is typically in the range from 2000 to 8000 g/24 h*m$^2$, preferably in the range from 2000 to 5000 g/24 h*m$^2$ and most preferably in the range from 2000 to 4000 g/24 h*m$^2$.

The polyurethane foams exhibit good mechanical strength and high elasticity. Typically, maximum stress is greater than 0.2 N/mm$^2$ and maximum extension greater than 250%. Preferably, maximum extension is greater than 350%, most preferably greater than 400% (determined according to DIN 53504).

After drying, the thickness of the wound dressings is typically in the range from 0.1 mm to 50 mm, preferably in the range from 0.5 mm to 20 mm, more preferably in the range from 1 to 10 mm and most preferably in the range from 1 to 5 mm.

The wound dressings can moreover be adhered, laminated or coated to with further materials, for example materials based on hydrogels, (semi-) permeable films, coatings, hydrocolloids or other foams.

If appropriate, a sterilizing step can be included in the process of the present invention. It is similarly possible in principle for wound dressings obtainable by the process of the present invention to be sterilized after they have been produced. Conventional sterilizing processes are used where sterilization is effected by thermal treatment, chemical substances such as ethylene oxide or irradiation with gamma rays for example.

It is likewise possible to add, incorporate or coat with antimicrobially or biologically active components which for example have a positive effect with regard to wound healing and the avoidance of germ loads.

Preferred active components of the aforementioned kind are those from the group consisting of antiseptics, growth factors, protease inhibitors and nonsteroidal anti-inflammatories/opiates.

In a preferred embodiment of the present invention, the active component comprises an antiseptic biguanide and/or its salt, preferably the hydrochloride.

Biguanides are compounds derived from biguanide ($C_2H_7N_5$), in particular its polymers. Antiseptic biguanides are biguanides that have an antimicrobial effect, i.e. act as bacteriostats or preferably as bactericides. The compounds in question preferably have a broad effect against many bacteria and can be characterized by a minimal microbicidal concentration (MMC, measured in the suspension test) of at least 0.5 μg/ml, preferably at least 12 or at least 25 μg/ml with regard to E. coli.

A preferred antiseptic biguanide according to this invention is poly(imino[iminocarbonyl]iminopolymethylene), the use of poly(hexamethylene)-biguanide (PHMB), also known as polyhexanide, as antiseptic biguanide being particularly preferred.

The term "antiseptic biguanides" according to this invention also comprehends metabolites and/or prodrugs of antiseptic biguanides. Antiseptic biguanides can be present as racemates or pure isoforms.

The foamed articles of polyurethane foams or the compositions according to the present invention preferably contain antiseptic biguanide and/or its salt, preferably the hydrochloride, in a concentration of 0.01% to 20% by weight, the concentration of 0.1% to 5% by weight being particularly advantageous. The biguanide may have any desired molecular weight distribution.

All the references described above are incorporated by reference in their entireties for all useful purposes.

While there is shown and described certain specific structures embodying the invention, it will be manifest to those skilled in the art that various modifications and rearrangements of the parts may be made without departing from the spirit and scope of the underlying inventive concept and that the same is not limited to the particular forms herein shown and described.

EXAMPLES

Unless indicated otherwise, all percentages are by weight.
Unless indicated otherwise, all analytical measurements relate to temperatures of 23° C.
Solids contents were determined in accordance with DIN-EN ISO 3251.
NCO contents were, unless expressly mentioned otherwise, determined volumetrically in accordance with DIN-EN ISO 11909.
Free NCO groups were monitored by IR spectroscopy (band at 2260 cm$^{-1}$).

The reported viscosities were determined by rotary viscometry in accordance with DIN 53019 at 23° C. using a rotary viscometer from Anton Paar Germany GmbH, Ostfildern, Germany.

Substances and Abbreviations Used:
Diaminosulphonate: $NH_2-CH_2CH_2-NH-CH_2CH_2-SO_3Na$ (45% in water)
Desmophen® C2200: polycarbonate polyol, OH number 56 mg KOH/g, number average molecular weight 2000 g/mol (Bayer MaterialScience AG, Leverkusen, Germany)
PolyTHF® 2000: polytetramethylene glycol polyol, OH number 56 mg KOH/g, number average molecular weight 2000 g/mol (BASF AG, Ludwigshafen, Germany)
PolyTHF® 1000: polytetramethylene glycol, OH number 112 mg KOH/g, number average molecular weight 1000 g/mol (BASF AG, Ludwigshafen, Germany)
LB 25 polyether: monofunctional polyether based on ethylene oxide/propylene oxide, number average molecular weight 2250 g/mol, OH number 25 mg KOH/g (Bayer Material Science AG, Leverkusen, Germany)
Pluronic® PE 6800: EO/PO block copolymer (BASF AG, Ludwigshafen, Germany)

The determination of the average particle sizes (the number average is reported) of the polyurethane dispersions was carried out using laser correlation spectroscopy (instrument: Malver Zetasizer 1000, Malver Inst. Limited).

Example 1

Polyurethane Dispersion 1

987.0 g of PolyTHF® 2000, 375.4 g of PolyTHF® 1000, 761.3 g of Desmophen® C2200 and 44.3 g of LB 25 polyether were heated to 70° C. in a standard stirring apparatus. Then, a mixture of 237.0 g of hexamethylene diisocyanate and 313.2 g of isophorone diisocyanate was added at 70° C. in the course of 5 min and the mixture was stirred at 120° C. until the theoretical NCO value was reached. The ready-produced prepolymer was dissolved with 4830 g of acetone and, in the process, cooled down to 50° C. and subsequently admixed with a solution of 25.1 g of ethylenediamine, 116.5 g of isophoronediamine, 61.7 g of diaminosulphonate and 1030 g of water metered in over 10 min. The mixture was subsequently stirred for 10 min. Then, a dispersion was formed by addition of 1250 g of water. This was followed by removal of the solvent by distillation under reduced pressure.
The white dispersion obtained had the following properties:
Solids content: 61%
Particle size (LKS): 312 nm
Viscosity (viscometer, 23° C.): 241 mPas
pH (23° C.): 6.02

Example 2

Polyurethane Dispersion 2

223.7 g of PolyTHF® 2000, 85.1 g of PolyTHF® 1000, 172.6 g of Desmophen® C2200 and 10.0 g of LB 25 polyether were heated to 70° C. in a standard stirring apparatus. Then, a mixture of 53.7 g of hexamethylene diisocyanate and 71.0 g of isophorone diisocyanate was added at 70° C. in the course of 5 min and the mixture was stirred at 120° C. until the theoretical NCO value was reached. The ready-produced prepolymer was dissolved with 1005 g of acetone and, in the process, cooled down to 50° C. and subsequently admixed with a solution of 5.70 g of ethylenediamine, 26.4 g of isophoronediamine, 9.18 g of diaminosulphonate and 249.2 g of water metered in over 10 min. The mixture was subsequently stirred for 10 min. Then, a dispersion was formed by addition of 216 g of water. This was followed by removal of the solvent by distillation under reduced pressure.

The white dispersion obtained had the following properties:
Solids content: 63%
Particle size (LKS): 495 nm
Viscosity (viscometer, 23° C.): 133 mPas
pH (23° C.): 6.92

Example 3

Polyurethane Dispersion 3

987.0 g of PolyTHF® 2000, 375.4 g of PolyTHF® 1000, 761.3 g of Desmophen® C2200 and 44.3 g of LB 25 polyether were heated to 70° C. in a standard stirring apparatus. Then, a mixture of 237.0 g of hexamethylene diisocyanate and 313.2 g of isophorone diisocyanate was added at 70° C. in the course of 5 min and the mixture was stirred at 120° C. until the theoretical NCO value was reached. The ready-produced prepolymer was dissolved with 4830 g of acetone and, in the process, cooled down to 50° C. and subsequently admixed with a solution of 36.9 g of 1,4-diaminobutane, 116.5 g of isophoronediamine, 61.7 g of diaminosulphonate and 1076 g of water metered in over 10 min. The mixture was subsequently stirred for 10 min. Then, a dispersion was formed by addition of 1210 g of water. This was followed by removal of the solvent by distillation under reduced pressure.

The white dispersion obtained had the following properties:
Solids content: 59%
Particle size (LKS): 350 mm
Viscosity (viscometer, 23° C.): 126 mPas
pH (23° C.): 7.07

Example 4

Polyurethane Dispersion 4

201.3 g of PolyTHF® 2000, 76.6 g of PolyTHF® 1000, 155.3 g of Desmophen® C2200, 2.50 g of 1,4-butanediol and 10.0 g of LB 25 polyether were heated to 70° C. in a standard stirring apparatus. Then, a mixture of 53.7 g of hexamethylene diisocyanate and 71.0 g of isophorone diisocyanate was added at 70° C. in the course of 5 min and the mixture was stirred at 120° C. until the theoretical NCO value was reached. The ready-produced prepolymer was dissolved with 1010 g of acetone and, in the process, cooled down to 50° C. and subsequently admixed with a solution of 5.70 g of ethylenediamine, 26.4 g of isophoronediamine, 14.0 g of diaminosulphonate and 250 g of water metered in over 10 min. The mixture was subsequently stirred for 10 min. Then, a dispersion was formed by addition of 243 g of water. This was followed by removal of the solvent by distillation under reduced pressure.

The white dispersion obtained had the following properties:
Solids content: 62%
Particle size (LKS): 566 nm
Viscosity (viscometer, 23° C.): 57 mPas
pH (23° C.): 6.64

Example 5

Polyurethane Dispersion 5

201.3 g of PolyTHF® 2000, 76.6 g of PolyTHF® 1000, 155.3 g of Desmophen® C2200, 2.50 g of trimethylolpropane and 10.0 g of LB 25 polyether were heated to 70° C. in a standard stirring apparatus. Then, a mixture of 53.7 g of hexamethylene diisocyanate and 71.0 g of isophorone diisocyanate was added at 70° C. in the course of 5 min and the mixture was stirred at 120° C. until the theoretical NCO value was reached. The ready-produced prepolymer was dissolved with 1010 g of acetone and, in the process, cooled down to 50° C. and subsequently admixed with a solution of 5.70 g of ethylenediamine, 26.4 g of isophoronediamine, 14.0 g of diaminosulphonate and 250 g of water metered in over 10 min. The mixture was subsequently stirred for 10 min. Then, a dispersion was formed by addition of 293 g of water. This was followed by removal of the solvent by distillation under reduced pressure.

The white dispersion obtained had the following properties:
Solids content: 56%
Particle size (LKS): 440 nm
Viscosity (viscometer, 23° C.): 84 mPas
pH (23° C.): 6.91

Example 6

Polyurethane Dispersion 6

1072 g of PolyTHF® 2000, 407.6 g of PolyTHF® 1000, 827 g of Desmophen® C2200 and 48.1 g of LB 25 polyether were heated to 70° C. in a standard stirring apparatus. Then, a mixture of 257.4 g of hexamethylene diisocyanate and 340 g of isophorone diisocyanate was added at 70° C. in the course of 5 min and the mixture was stirred at 120° C. until the theoretical NCO value was reached. The ready-produced prepolymer was dissolved with 4820 g of acetone and, in the process, cooled down to 50° C. and subsequently admixed with a solution of 27.3 g of ethylenediamine, 126.5 g of isophoronediamine, 67.0 g of diaminosulphonate and 1090 g of water metered in over 10 min. The mixture was subsequently stirred for 10 min. Then, a dispersion was formed by addition of 1180 g of water. This was followed by removal of the solvent by distillation under reduced pressure.

The white dispersion obtained had the following properties:
Solids content: 60%
Particle size (LKS): 312 nm
Viscosity (viscometer, 23° C.): 286 mPas
pH (23° C.): 7.15

Comparative Example 1

Polyurethane dispersion, not inventive (no sulphonate groups, just hydrophilicization through nonionic groups and carboxylate groups)

Example 1 is repeated except that the diaminosulphonate was replaced by an equimolar amount of a carboxylato-containing component:

206.8 g of PolyTHF® 2000, 78.7 g of PolyTHF® 1000, 159.5 g of Desmophen® C2200 and 9.3 g of LB 25 polyether were heated to 70° C. in a standard stirring apparatus. Then, a mixture of 49.7 g of hexamethylene diisocyanate and 65.6 g of isophorone diisocyanate was added at 70° C. in the course of 5 min and the mixture was stirred at 120° C. until the theoretical NCO value was reached. The ready-produced prepolymer was dissolved with 1010 g of acetone and, in the process, cooled down to 50° C. and subsequently admixed with a solution of 5.3 g of ethylenediamine, 24.4 g of isophoronediamine, 11.9 g of KV 1386 (40% aqueous solution of the sodium salt of N-(2-aminoethyl)-β-alanine, BASF AG, Ludwigshafen, Germany) and 204 g of water metered in over 10 min. The mixture was subsequently stirred for 10 min. Then, a dispersion was formed by addition of 235 g of water. This was followed by removal of the solvent by distillation under reduced pressure. A total of 250 g of water had to be added because of the high viscosity.

The white dispersion obtained had the following properties:
Solids content: 47%
Particle size (LKS): 918 nm
Viscosity (viscometer, 23° C.): 162 mPas
pH (23° C.): 7.22

Owing to the comparatively high average particle size of >900 nm and contrary to the purely sulphonate-hydrophilicized dispersions, sedimentation was observed to ensue within a few days, making further processing into foams difficult.

Comparative Example 2

Polyurethane dispersion, not inventive (no sulphonate groups, just hydrophilicization through nonionic groups and carboxylate groups)

Comparative Example 1 was repeated except that the amount of the carboxylato-containing hydrophilicizing component was increased by 50% (while keeping the degree of chain extension the same).

206.8 g of PolyTHF® 2000, 78.7 g of PolyTHF® 1000, 159.5 g of Desmophen® C2200 and 9.3 g of LB 25 polyether were heated to 70° C. in a standard stirring apparatus. Then, a mixture of 49.7 g of hexamethylene diisocyanate in 65.6 g of isophorone diisocyanate was added at 70° C. in the course of 5 min and the mixture was stirred at 120° C. until the theoretical NCO value was reached. The ready-produced prepolymer was dissolved with 1010 g of acetone and, in the process, cooled down to 50° C. and subsequently admixed with a solution of 5.3 g of ethylenediamine, 21.8 g of isophoronediamine, 17.9 g of KV 1386 (40% aqueous solution of the sodium salt of N-(2-aminoethyl)-β-alanine, BASF AG, Ludwigshafen, Germany) and 204 g of water metered in over 10 min. The mixture was subsequently stirred for 10 min. Then, a dispersion was formed by addition of 235 g of water. This was followed by removal of the solvent by distillation under reduced pressure.

The white dispersion obtained had the following properties:
Solids content: 52.2%
Particle size (LKS): 255 nm
Viscosity (viscometer, 23° C.): 176 mPas
pH (23° C.): 8.31

This polyurethane dispersion had a lower average particle size but a somewhat higher pH than Comparative Example 2. Further processing to foams was distinctly more difficult than with purely sulphonate-hydrophilicized dispersions.

Examples 7-9

Production of Crosslinked Foams and Testing for Water Resistance

The Table 1 amounts of the polyurethane dispersion 2 (Example 2), of the foam auxiliary Pluronic® 6800 and of the crosslinker were mixed and frothed by means of a commercially available hand stirrer (stirrer made of bent wire) in the course of 10 minutes to a foam volume of 500 ml. Thereafter, the foams were deleted on a release paper (wet film thickness 4 mm). The foams were dried for 20 min. at 120° C. and for 10 min. at 150° C. Clean white hydrophilic foams having good mechanical properties and fine pore structure were obtained without exception.

The crosslinked foams also displayed good water resistance.

TABLE 1

| Example | Amount [g] Polyurethane dispersion 2 | Pluronic ® PE 6800 | Crosslinker | Water resistance[4] | Hydrophilicity[5] |
|---|---|---|---|---|---|
| 7 | 120 | 13.3 | 0.76[1] | good | <1 sec. |
| 8 | 120 | 13.3 | 0.76[2] | good | <1 sec. |
| 9 | 120 | 13.3 | 0.76[3] | good | <1 sec. |

[1] Acrafix ML (hexamethoxymethylmelamine, Lanxess AG, Leverkusen, Germany);
[2] Bayhydur 305 (nonionically hydrophiliazed polyisocyanate based on hexamethylene diisocyanate, NCO content: 16.2%, BayerMaterialScience AG, Leverkusen, Germany);
[3] Bayhydur 3100 (nonionically hydrophiliazed polyisocyanate based on hexamethylene diisocyanate, NCO content: 17.4% BayerMaterialScience AG, Leverkusen, Germany;
[4] 18 h immersion of a 5 × 5 cm foam in distilled water at 37° C., thereafter comparative testing of tongue tear resistance (classification: low, medium, good);
[5] time to fully absorb a drop of water (as a measure of the hydrophilicity of the foams)

Comparative Examples 3

Production of an Uncrosslinked Foam and Testing for Water Resistance

An uncrosslinked foam was produced in the same way as described in Examples 7-9, i.e. no crosslinker was used. The uncrosslinked foam had a distinctly lower water resistance (classification: "low") than the crosslinked foams of Examples 7-9.

The invention claimed is:

1. A process for producing foamed articles comprising frothing and drying a composition comprising aqueous polyurethane dispersions (I) anionically hydrophilicized by means of sulphonate groups and a crosslinker (II);
wherein said polyurethane dispersion (I) is prepared by
A) producing a isocyanate-functional prepolymer from
   A1) organic polyisocyanates;
   A2) polymeric polyols having number-average molecular weights in the range from 400 to 8000 g/mol and OH functionalities in the range from 1.5 to 6; and
   A3) optionally hydroxyl-functional compounds having molecular weights in the range from 62 to 399 g/mol; and
   A4) optionally isocyanate-reactive, anionic or potentially anionic and optionally nonionic hydrophilicizing agents;
and
B) wholly or partly reacting the free NCO groups of said isocyanate-functional prepolymer
   B1) optionally with amino-functional compounds having molecular weights in the range from 32 to 400 g/mol; and
   B2) with an alkali metal salt of a mono- or diamino sulphonic acid
by chain extension;
wherein said isocyanate-functional prepolymer is dispersed in water before, during or after step B),
wherein at least partial chemical crosslinking occurs during frothing and/or drying, and wherein said crosslinkers (II) are selected from the group consisting of unblocked, optionally hydrophilicized polyisocyanates; amide- and amine-formaldehyde resins; phenolic resins; aldehyde and ketone resins; resols; furan resins; urea resins; carbamidic ester resins; triazine resins; melamine resins; benzoguanamine resins; cyanamide resins; and aniline resins, and
wherein the foamed article is a wound dressing.

2. The process of claim 1, wherein said polyurethane dispersion (I) are anionically hydrophilicized by sulphonate groups only.

3. The process of claim 2, wherein said sulphonate groups have alkali metal cations as counter-ions.

4. The process of claim 1, wherein said polyurethane dispersion (I) comprise 0.1 to 15 milliequivalents per 100 g of solid resin of anionic or potentially anionic groups based on solid resin.

5. The process of claim 1, wherein said polyurethane dispersion (I) have solids contents in the range of from 55% to 65% by weight based on the polyurethane present therein.

6. The process of claim 1, wherein said crosslinkers (II) are unblocked polyisocyanates.

7. The process of claim 6, wherein said unblocked polyisocyanates are hydrophilicized.

8. The process of claim 1, further comprising auxiliary and additive materials (III).

9. The process of claim 8, wherein said auxiliary and additive materials (III) are foam formers and stabilizers selected from the group consisting of fatty acid amides, sulphosuccinamides, hydrocarbyl sulphonates or sulphates, alkyl polyglycosides, EO-PO block copolymers, fatty acid salts, and combinations thereof.

10. The process of claim 9, wherein said foam formers and stabilizers are EO-PO block copolymers.

11. The process of claim 1, further comprising active components selected from the group consisting of antiseptics, growth factors, protease inhibitors, and nonsteroidal anti-inflammatories/opiates.

12. The process of claim 11, wherein said active component is an antiseptic biguanide and/or its salt.

13. A foamed article prepared by the process of claim 1.

14. The foamed article of claim 13, wherein said foamed article has a microporous, open-cell structure and a density of below 0.4 g/cm$^3$ in the dried state.

15. The foamed article of claim 13, wherein said foamed article has a DIN EN 13726-1 Part 3.2 physiological saline absorbency in the range from 100 to 1500% (mass of liquid taken up, based on the mass of dry foam) and a DIN EN 13726-2 Part 3.2 water vapour transmission rate in the range from 2000 to 8000 g/24 h*m$^2$.

16. The foamed article of claim 13, wherein said foamed article further comprises an active component.

17. The foamed article of claim 13, wherein said foamed article is a wound dressing.

18. The process of claim 1, wherein the foamed article has a microporous, open-cell structure and a density of below 0.4 g/cm$^3$ in the dried state.

19. The process of claim 1, wherein the foamed article has a DIN EN 13726-1 Part 3.2 physiological saline absorbency in the range from 100 to 1500% (mass of liquid taken up, based on the mass of dry foam) and a DIN EN 13726-2 Part 3.2 water vapour transmission rate in the range from 2000 to 8000 g/24 h*m$^2$.

20. The process of claim 1, wherein the foamed article further comprises an active component.

21. The process of claim 1, wherein component B2) is selected from the group consisting of salts of 2-(2-aminoethylamino)ethanesulphonic acid, ethylenediaminepropylsulphonic acid, ethylenediaminebutylsulphonic acid, 1,2- or 1,3-propylenediamine-β-ethylsulphonic acid, taurine and salt of cyclohexylaminopropanesulphonic acid.

22. The process of claim 1, wherein components A1) to A4) and B1) to B2) are used in the following amounts:
  10% to 30% by weight of component A1),
  65% to 85% by weight of A2),
  0.5% to 14% by weight of the sum total of components A3) and B1)
  0.1% to 13.5% by weight of the sum total of the components A4) and B2), with 0.5 to 3.0% by weight of anionic or potentially anionic hydrophilicizing agents from A4) and/or B2) being used, based on the total amount of components A1) to A4) and B1) to B2), and wherein the total amounts of A1) to A4) and B1) to B2) do not exceed a 100% by weight.

\* \* \* \* \*